Figures 1, 2:
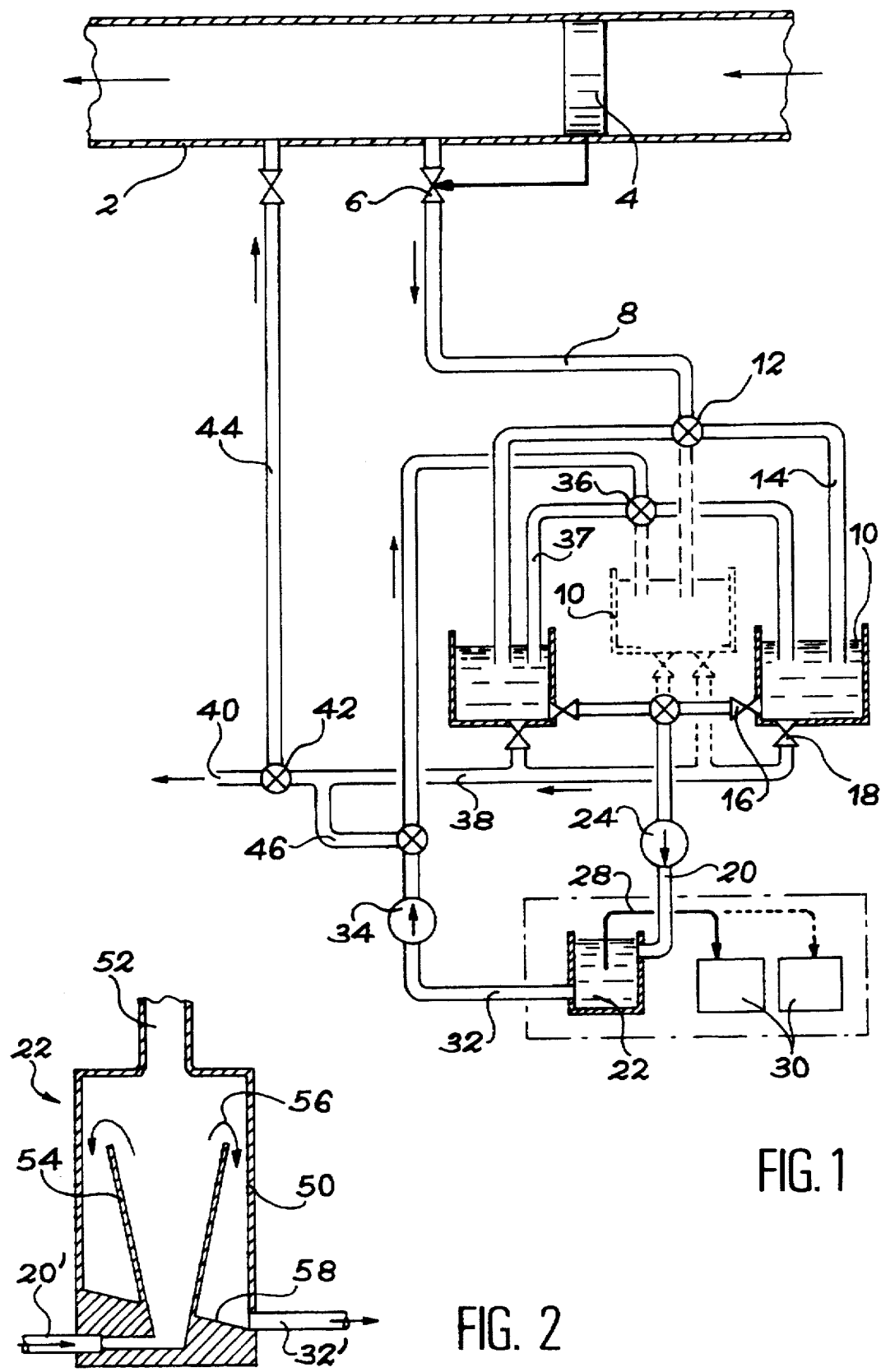

United States Patent [19]

De Bruyne et al.

[11] Patent Number: 5,723,093
[45] Date of Patent: Mar. 3, 1998

[54] APPARATUS FOR THE CONTINUOUS SAMPLING AND ANALYSIS OF A LIQUID EFFLUENT

[75] Inventors: Thierry De Bruyne, Fresnes; Eric Leduc, Breuillet; Thierry Juhel, Massy Palaiseau, all of France

[73] Assignee: Commissariat a L'Energie Atomique, France

[21] Appl. No.: 617,786
[22] PCT Filed: Jul. 18, 1995
[86] PCT No.: PCT/FR95/00963
 § 371 Date: Aug. 5, 1996
 § 102(e) Date: Aug. 5, 1996
[87] PCT Pub. No.: WO96/02818
 PCT Pub. Date: Feb. 1, 1996

[30] Foreign Application Priority Data

Jul. 19, 1994 [FR] France .................. 94 08909

[51] Int. Cl.[6] .................................................. G01N 1/20
[52] U.S. Cl. .................. 422/81; 422/68.1; 422/100; 436/43; 436/52; 436/174; 436/180; 73/863; 73/863.31; 73/863.81
[58] Field of Search ............... 422/68.1, 81, 100, 422/103; 436/43, 52, 174, 179, 180; 73/863, 863.31, 863.81

[56] References Cited

U.S. PATENT DOCUMENTS

| | | | |
|---|---|---|---|
| 3,798,972 | 3/1974 | Collins, Jr. .................. | 73/422 |
| 3,929,411 | 12/1975 | Takano et al. ................ | 436/180 |
| 4,795,713 | 1/1989 | Koop et al. ................... | 436/175 |
| 4,800,763 | 1/1989 | Hakkers et al. ............... | 73/863 |
| 4,873,057 | 10/1989 | Robertson et al. ............ | 422/75 |
| 5,073,505 | 12/1991 | Nalette et al. ................ | 436/178 |
| 5,077,017 | 12/1991 | Gorin et al. .................. | 422/100 |
| 5,101,670 | 4/1992 | Steger et al. ................. | 73/863.03 |

FOREIGN PATENT DOCUMENTS

| | | |
|---|---|---|
| 0075977 | 4/1983 | European Pat. Off. . |
| 0281171 | 9/1988 | European Pat. Off. . |
| 1441661 | 9/1966 | France . |
| 2249320 | 5/1975 | France . |
| 2042471 | 9/1980 | United Kingdom . |

*Primary Examiner*—Long V. Le
*Attorney, Agent, or Firm*—Hayes, Soloway, Hennessey, Grossman & Hage, P.C.

[57] ABSTRACT

The invention relates to an apparatus for continuously sampling and analyzing a liquid effluent, e.g. from an industrial installation, thereby permitting the rapid detection of pollution in a discharge. The apparatus comprises a valve (6) for permanently deflecting part of the liquid effluent to be analyzed in the direction of first distribution valve (12), at least two provisional storage tanks (10), connected to the inlet of a sampling cell (22), and capillary tube (28) for taking a sample from said sampling cell (22) and passing it to at least one measuring device (30). The distribution valve (12) is designed so as successively to fill provisional storage tanks (10), the storage tanks (10) being emptied, in the order in which they were filled, into the sampling cell (22) when the latter is empty.

19 Claims, 1 Drawing Sheet

APPARATUS FOR THE CONTINUOUS SAMPLING AND ANALYSIS OF A LIQUID EFFLUENT

The invention relates to an apparatus for continuously sampling and analyzing a liquid effluent, e.g. from an industrial installation.

Most industrial installations discharge effluents, which are subject to ever stricter monitoring by the public authorities and to ever stricter environmental discharge standards. More particularly in industrial chemical treatment plants (e.g. surface treatment), in chemical industries or in nuclear centres, the quantity of anions and cations present in the industrial effluents must be measurable in both a precise and time-regular manner.

At present, e.g. in a nuclear centre, all water from different buildings within the centre is collected in a collecting basin with a capacity of about 100 m$^3$, followed by the treatment thereof. Such water comes both from sanitary installations and laboratories and e.g. consists of water used in production processes, water used in cooling or recycled water, i.e. water used in e.g. heat exchangers. In the collecting basin located within the water treatment station, said water undergoes a flocculation treatment with the aid of iron sulphate and lime, followed by the settling of the sludge. All these operations are performed accompanied by stirring, e.g. by injecting air bubbles. The aim of this treatment is to eliminate the heavy metals. Following this treatment, the water is collected in a secondary basin, where analysis takes place, prior to the discharge thereof into the environment. This analysis is usually performed manually on the basis of one or two daily sampling operations carried out in said secondary basin. Each sample is analyzed, e.g. using a plasma torch coupled to a mass spectrometer. These methods make it possible to measure several elements present in a sample.

This effluent discharge monitoring procedure is obviously very imprecise, because it does not take account of the evolution of the composition of the discharges during the day, which can sometimes be very important. It also has a relatively long reaction time between the moment when a polluted effluent enters the secondary basin and the moment when the pollution is detected.

The evolution of effluent treatment methods and in particular the appearance of the so-called "streamline" treatment has led to a different procedure being adopted in the checking of discharges. Thus, spent water from different points (e.g. different buildings within a nuclear centre) will be collected in a buffer basin, where all the aforementioned water treatment operations will be carried out and then the treated water from the different buffer basins will be collected in a storage basin prior to discharge into the environment. The checking and analysis of the effluents will take place in a streamline manner, i.e. in the pipe between one of the buffer basins and the storage basin and this will be performed continuously. It is therefore desirable to develop an apparatus making it possible to very rapidly and precisely detect a variation in the concentration of elements polluting a discharge, so as to be able to immediately isolate the polluted effluent and recycle it in the buffer basin for a second water treatment.

At present, the apparatuses used for the analysis of industrial effluents, such as ionic chromatographic equipment or capillary electrophoresis equipment do not permit working on a continuous sample of said effluent. In fact, they are designed to function on samples collected from test tubes and the latter are placed on a turntable so that said samples are brought in turn in front of the sampling means thereof. This leads to an extremely long, manual manipulation incompatible with a continuous effluent monitoring. The object of the invention is to solve this problem.

The invention therefore relates to an apparatus for the continuous sampling and analysis of a liquid effluent.

According to the features of the invention, said apparatus comprises:

means for permanently deflecting part of the liquid effluent flow to be analyzed in the direction of first distribution means, at least two provisional storage tanks, first means for draining each of the provisional storage tanks, connected to the inlet of a sampling cell, means for taking a sample in said sampling cell and directing it to at least one measuring device and means for emptying said sampling cell, said first distribution means being designed so as to successively fill an empty, provisional storage tank and said draining means are designed so as to successively empty the full, provisional storage tanks, in the order in which they were filled, in the interior of said sampling cell, when the latter is empty.

This apparatus permits the taking of continuous samples and therefore no information relating to a possible pollution of the liquid effluent is lost. When using the apparatus, the different provisional storage tanks are successively filled and then drained within the sampling cell, where a sample representing a minute portion of said volume is taken and is then treated by the analysis apparatus or apparatuses. The remainder of the liquid volume which has circulated in the sampling cell is discharged to the outside or stored for subsequent analyses. Thus, if a pollution is detected, it is possible to perform more accurate, complimentary analyses or relating to a larger number of chemical elements.

Several different sampling operations can also be carried out for analysis by different measuring apparatuses or devices, as a function of the nature of the pollution which it is wished to detect.

The number of provisional storage tanks is adapted as a function of their filling time and the time necessary for filling and draining the sampling cell and for the taking of the sample and its measurement.

Advantageously, the apparatus according to the invention also comprises:

second distribution means connected to the outlet of the sampling cell and permitting the emptying of the liquid contained in said cell into the provisional storage tank from which said liquid has come, prior to said storage tank being filled again, at least one pump for ensuring the circulation of the liquid effluent and second means for draining each of the provisional storage tanks connected to an evacuation pipe.

As a result of the features of the invention, it is possible to recirculate the liquid effluent within the sampling cell and thus take a second sample. It is therefore also possible as a result of this to better homogenize the sampled liquid. Finally, the evacuation pipe can be connected to a sampling device with a view to the storage and keeping of samples, so as not to lose information. This is e.g. the case when the measurement performed exceeds a threshold value.

The evacuation pipe can also be connected to a pipe in which circulates the initial liquid effluent to be analyzed and this is downstream of the aforementioned deflection means. This is possible, because only the very small liquid fractions sampled and then brought into the measuring device is possibly contaminated by chemical reagents, whereas virtually all the deflected effluent is unpolluted.

Preferably, the means for permanently deflecting part of the liquid effluent flow are constituted by a solenoid valve or a proportional pump, said means being dependent on a flowmeter measuring the liquid effluent flow, so as to sample a constant proportion of the latter. Thus, this apparatus makes it possible to collect a representative portion of the flow, in the hypothesis that the latter is homogeneous and has a constant composition.

According to a preferred embodiment of the invention, the first and second distribution means are constituted by a distributing valve. In this case, the provisional storage tanks are fixed and the distributing valve makes it possible to direct the deflected liquid effluent flow in turn in the direction of the provisional storage tanks. However, according to a not shown embodiment, the distribution means could be formed by mobile, provisional storage tanks moving successively in front of the outlet orifice of a pipe connected to the deflection means.

According to a preferred embodiment of the invention, the measuring device is a capillary electrophoresis device making it possible to perform a rapid measurement in about ten minutes.

The invention is described in greater detail hereinafter relative to nonlimitative embodiments and with reference to the attached drawings, wherein show:

FIG. 1 A diagram illustrating the apparatus for the continuous sampling and analysis of a liquid effluent according to the invention.

FIG. 2 A sectional view of-a preferred embodiment of the sampling cell installed in the apparatus according to the invention.

As illustrated by FIG. 1, the apparatus according to the invention comprises a main pipe 2 in which flows the liquid effluent to be analyzed. This main pipe 2 is provided with a flowmeter 4 and means 6 for permanently deflecting part of the liquid effluent flow to be analyzed in the direction of a deflection pipe 8. Preferably, the means 6 are constituted by a solenoid valve or a proportional pump and are dependent on the flowmeter 4, as is illustrated by an arrow in FIG. 1. Thus, the means 6 make it possible to sample a constant proportion of the liquid effluent flow in the main pipe 2.

The apparatus according to the invention also comprises at least two provisional storage tanks 10. Preferably, each storage tank 10 is provided with a stirrer 11 (magnetic or propeller type). Moreover, the deflection pipe 8 is connected, via first distribution means 12 and distribution pipes 14, to each of the provisional storage tanks.

Each provisional storage tank 10 is equipped with first and second draining means 16 and 18 and generally constituted by a valve. The valve 16 is placed on a multibranch inlet pipe 20, connecting each provisional storage tank 10 to a sampling cell 22. The inlet pipe 20 is advantageously provided with a pump 24, but the latter is not necessary. A capillary tube 28 which can be immersed in said sampling cell 22 makes it possible to take samples at regular intervals and pass the minute quantities sampled to at least one measuring device 30.

The sampling cell 22 is emptied as soon as the sample or samples have been taken and is then filled again. In the simplest embodiment illustrated in FIG. 1, said sampling cell 22 is filled in its upper part and emptied in its lower part by means of an outlet pipe 32. However, other embodiments of said cell are possible and one of them is described hereinafter.

The outlet or discharge pipe 32, which is advantageously equipped with a pump 34 is connected to the second distribution means 36. The latter are generally formed by a distributing valve making it possible to drain the liquid contained in the sampling cell 22 into a distribution pipe 37 and then into the provisional storage tank 10 from which said liquid came. The inlet pipe 20, the sampling cell 22, the outlet pipe 32, the second distribution means 36 and the distribution pipe 37 consequently form a circulation loop for the deflected liquid.

The valves 18 of each provisional storage tank 10 are installed on an evacuation pipe 38, which can be connected at its end 40, e.g. to a not shown, sampling apparatus making it possible to store samples representative of the liquid flow for subsequent analysis purposes. The evacuation pipe 38 comprises a valve 42 located at the intersection between said pipe 38 and a return pipe 44. This return pipe 44 connects the evacuation pipe 38 to the main pipe 2, downstream of the deflection valve 6. The discharge pipe 32 can also have a branch 46 permitting its connection to the evacuation pipe 38.

The operation of the apparatus according to the invention will now be described. The deflection means 6 continuously sample a fraction of the liquid effluent to be analyzed and direct said deflected effluent to the distributing valve 12. The latter is controlled so as to direct the effluent to one of the distribution pipes 14 and a first, corresponding storage tank 10. When the first tank is full, a not shown detector acts on the distributing valve 12, so as to modify its position so as to authorize the filling of a second, provisional storage tank 10. During this time, the valve 16 is open so as to fill the sampling cell 22. When the latter is full, one or more liquid samples are taken by the capillary tube 28. The sampling cell 22 is then emptied and its content is directed either directly to the main pipe 2, by the pipes 32, 46 and 44, either to the end 40 of the evacuation pipe 38, or again to the first storage tank 10 from which it came. During this time, as soon as the sampling cell 22 is empty and the second storage tank 10 is full, the second tank is emptied into the sampling cell 22, where the aforementioned operations take place. In parallel, a third or nth provisional storage tank 10 is filled. These tanks are emptied in the order of their filling into the sampling cell 22. When all the storage tanks have been filled once and then emptied, they will successively undergo this operation again.

When the content of the sampling cell 22 is not directly evacuated, but is instead returned a second time into the storage tank 10 from which it came, it is again brought into the sampling cell 22 for a further sampling operation, prior to the emptying into said cell of the content of another storage tank 10. This leads to the entraining of the few liquid droplets which may have remained in the inlet pipe 20. Therefore the measurements performed are more reliable.

According to an embodiment of the invention, the measuring device 30 is a capillary electrophoresis device, which has the advantage of performing an analysis in about 10 minutes. In this case, the sampling cell 22 has the structure illustrated in FIG. 2. This cell has a cubic or cylindrical shape defined by the walls 50. In its upper part it has an opening 52 for the passage of a not shown capillary tube 28. The cell 22 is internally provided with an "overflow" dish 54, e.g. in the shape of a truncated cone, whose base is connected to an inlet pipe 20'. The height of said dish 54 is less than the height of the cell 22, so that the liquid penetrating the pipe 20' progressively rises in said dish and overflows within the cell 22, as illustrated by the arrows 56. The sampling cell 22 also has at its base means 5B (e.g. an inclined plane) permitting the collection of the liquid which has overflown the dish 54 and passes the same to a discharge pipe 32'.

The special shape of said sampling cell makes it possible to avoid liquid retentions in the cell and facilitates the flow of fluid.

An exemplified embodiment will now be described.

EXAMPLE

The deflection valve 6 makes it possible to sample 1/2000 of the flow to be analyzed circulating in the main pipe 2. The apparatus comprises two provisional storage tanks 10 with a volume adapted to the maximum flow treated by the plant ($\approx$30 ml to 15 l) and having a flared shape. The flow of liquid within the apparatus is 160 ml/min. The volume of the sampling cell 22 is 4 ml. The first measuring apparatus 30 is a capillary electrophoresis apparatus used for the analysis of anions such as $Cl^-$, $SO_4^{2-}$, $Br^-$, $ClO_4^-$, $HGO_3^{13}$, $NO_2^-$, $NO_3^-$, $F^-$, $CrO_4^{2-}$, $HPO_4^{2-}$, $SCN^-$. The second measuring apparatus 30 is a cation ionic chromatography apparatus.

When the measuring apparatus is a capillary electrophoresis apparatus, the sampling cell 22 is advantageously installed on a riser, so as to be able to rise by a few dozen centimetres in a few seconds. The capillary tube 28 then serves as a siphoning tube. This makes it possible to very simply inject into the capillary electrophoresis apparatus a liquid volume representative of the deflected effluent.

We claim:

1. Apparatus for continuous sampling and analysis of a liquid effluent, comprising; a liquid effluent flow and first distribution means, means for permanently deflecting part of the liquid effluent flow to be analyzed through said first distribution means, at least two provisional storage tanks and a sampling cell, each containing an inlet and an outlet, first means for draining each of the provisional storage tanks, connected to said inlet of said sampling cell, means for withdrawing a sample from said sampling cell and transferring said sample to at least one measuring device, and means for emptying said sampling cell, wherein said first distribution means is designed so as successively to fill said provisional storage tanks, and said draining means are designed so as successively to empty said provisional storage tanks in the order in which said provisional storage tanks are filled, into said sampling cell when the latter is empty.

2. Apparatus for continuous sampling and analysis according to claim 1, and further comprising:

second distribution means connected to said outlet of the sampling cell for permitting the emptying of the liquid contained in said cell into said provisional storage tanks, from which said liquid came before said storage tank is filled again, at least one pump for circulating the liquid effluent, and second draining means for each of the provisional storage tanks connected to an evacuation pipe.

3. Apparatus according to claim 1, wherein the means for the permanent deflection of part of the liquid effluent flow are dependent on a flowmeter which measures a flow rate of said liquid effluent, so as to sample a constant proportion thereof.

4. Apparatus according to claim 3, wherein the means for deflecting part of the flow comprises a solenoid valve.

5. Apparatus according to claim 1, wherein the first distribution means comprises a distributing valve connecting the deflection means in turn to one of the provisional storage tanks.

6. Apparatus according to claim 2, wherein the second distribution means comprises a distributing valve connecting the outlet of the sampling cell in turn to one of the provisional storage tanks.

7. Apparatus according to claim 1, wherein the first draining means of the provisional storage tanks comprises a valve.

8. Apparatus according to claim 2, wherein the second draining means of the provisional storage tanks comprises a valve.

9. Apparatus according to claim 2, wherein a pump is placed between the outlet of the sampling cell and the second distribution means.

10. Apparatus according to claim 1, wherein the provisional storage tanks are equipped with stirrers.

11. Apparatus according to claim 2, wherein the evacuation pipe is connected to a main pipe, in which circulates the liquid effluent to be analyzed, downstream of the means for deflecting part of the flow.

12. Apparatus according to claim 2, wherein the outlet of the sampling cell is connected to the evacuation pipe by a branch.

13. Apparatus according to claim 1, wherein the measuring device comprises a capillary electrophoresis device.

14. Apparatus according to claim 1, wherein the sampling cell is internally provided with an overflow dish, whose base is connected to the inlet of the sampling cell and whose height is less than that of the cell, and including means for collecting the liquid which has overflown said dish connected to the outlet of the sampling cell.

15. Apparatus according to claim 2, wherein the provisional storage tanks are equipped with stirrers.

16. Apparatus according to claim 2, wherein the measuring device comprises a capillary electrophoresis device.

17. Apparatus according to claim 2, wherein the sampling cell is internally provided with an overflow dish, whose base is connected to the inlet of the sampling cell and whose height is less than that of the cell, and including means for collecting the liquid which has overflown said dish connected to the outlet of the sampling cell.

18. Apparatus according to claim 13, wherein the sampling cell is internally provided with an overflow dish, whose base is connected to the inlet of the sampling cell and whose height is less than that of the cell, and including means for collecting the liquid which has overflown said dish connected to the outlet of the sampling cell.

19. Apparatus according to claim 3, wherein the means for deflecting part of the flow comprises a proportional pump.

* * * * *